United States Patent [19]

Streli

[11] Patent Number: 4,565,193

[45] Date of Patent: Jan. 21, 1986

[54] PRONGED PLATE FOR RESETTING FRACTURED BONES

[76] Inventor: Elke Streli, Stelzhamerstrasse 2, A-4020 Linz, Austria

[21] Appl. No.: 531,905

[22] Filed: Sep. 12, 1983

[30] Foreign Application Priority Data

Sep. 13, 1982 [AT] Austria .................................. 3413/82

[51] Int. Cl.[4] ................................................ A61F 5/04
[52] U.S. Cl. .............................. 128/92 D; 128/92 BA
[58] Field of Search .................... 128/92 D, 92 E, 20, 128/92 B, 92 BA, 92 BB

[56] References Cited

U.S. PATENT DOCUMENTS

| | | | |
|---|---|---|---|
| 2,496,126 | 1/1950 | Habough | 128/92 BA |
| 3,824,995 | 7/1974 | Getscher et al. | 128/92 B |
| 3,998,217 | 12/1976 | Trumbull et al. | 128/20 |
| 4,120,298 | 10/1978 | Fixel | 128/92 D |
| 4,269,180 | 5/1981 | Dall et al. | 128/92 D |
| 4,364,382 | 12/1982 | Mennen | 128/92 D |
| 4,473,068 | 9/1984 | Oh | 128/92 D |

FOREIGN PATENT DOCUMENTS

| | | | |
|---|---|---|---|
| 1487486 | 5/1967 | France | 128/92 D |
| 982680 | 12/1982 | U.S.S.R. | 128/92 D |

Primary Examiner—Gene Mancene
Assistant Examiner—C. W. Shedd
Attorney, Agent, or Firm—Karl F. Ross; Herbert Dubno

[57] ABSTRACT

A pronged plate for fixing bone parts together at a bone fracture in the region of an articulation has prongs projecting transversely from one end of the plate, which is elongate to lie along a limb bone, and has perforations to receive securing screws to be screwed into the bone. To prevent the articular part of the bone from slipping off the prongs when loaded in use, the axes of the prongs are arranged to make an angle of about 20° with the plane which is perpendicular to the elongate part of the plate and contains the longitudinal axis of the plate.

13 Claims, 3 Drawing Figures

PRONGED PLATE FOR RESETTING FRACTURED BONES

FIELD OF THE INVENTION

The invention relates to a pronged plate for fixing bone parts together in position in the case of bone fractures in the region of an articulation, having prongs projecting transversely from one end of the plate and having apertures for receiving screws or the like.

BACKGROUND OF THE INVENTION

To reposition, i.e. reset, a bone in the case of a bone fracture in the region of an articulation, it is known to apply a plate to the surface of the fractured bone, which plate extends across the fracture, is formed at one end with transversely projecting prongs and is therefore called a pronged plate. The prongs are here inserted into the articular head and the plate itself is fixed by means of screws to the shaft of the bone. For bone fractures, pronged plates of this type have the function of fixing the bone parts against changes in position, to thus enable the fracture to heal with the bone parts in the correct position and additionally to accelerate the healing process.

In the pronged plates known from German Auslegeschrift No. 2,602,900, French Patent Specification No. 1,487,486 and French Published Application No. 2,064,530, the prongs extend approximately parallel to the perpendicular plane through the longitudinal axis of the plate, the prongs projecting from the plate part at an angle of about 70° to 120°. However, this is a disadvantage, inasmuch as there is a risk of the fragment of the articular head sliding off from the prongs when the bone is put under load. This is the case particularly if the bone parts have a porous, i.e. spongy structure, or there is crushed bone or the contact surface is small or there is little room available for fixing the plate by means of the prongs, as is the case, for example, with fractures in the region of the end remote from the body, i.e. the distal end, of radius bones.

OBJECT OF THE INVENTION

It is therefore an object of the invention to provide a pronged plate, with which the secure fixing of the bone parts in position is possible even in the cases listed above.

SUMMARY OF THE INVENTION

According to the invention, this is achieved when the axes of the prongs include angles of between 10° and 30°, preferably of about 20°, with a first plane which is generally perpendicular to the plate and includes the longitudinal axis of the plate. Such an alignment of the prongs prevents the articular part of the bone from sliding off the prongs.

Preferably, the prongs here enclose an angle of less than 90°, in particular an angle of 80°, with the plane approximately coinciding with the plate, i.e. a second plane including the axis but transverse to the first plane. In combination with a screw, which is likewise inserted in the articular part of the fragment, optimum fixing of the articular part of the plate can be achieved in this way.

According to further preferred features, the plate is formed with at least two and preferably with four prongs. Moreover, the plate can, over its entire longitudinal extent, have a width which steadily increases in the direction of the prongs, the width in the region of the prongs being at least 1.5 times, preferably three times, that in the region of the other end. This widening makes a large contact area with the bone parts at the site of fracture possible. In addition, the pronged plate can be bent outwards in its wider region. All these features lead to an adaptation of the widened part to the anatomical shape of the bones.

At least one apertures for receiving a screw which can be inserted into the articular part can be located in the region directly adjacent to the prongs. A screw providing additional fixing of position can be introduced through this perforation into the articular part. The external support at the site of fracture requires additional fixing in the form of bracing by means of the screw especially if the articular part has been crushed or if the structure of the bone in the region of fracture is particularly porous. Provided that this screw encloses an angle of between 45° and 20°, preferably of about 30°, with the prongs, the spongy bone fragments can become compressed and stabilised between the prongs and the plate.

Finally, if at least one of the apertures, preferably the aperture furthest away from the prongs, is shaped as a slot, fine adjustment of the pronged plate on the bone shaft is possible before final fixing.

A pronged plate according to the invention is described below in more detail with reference to an illustrative preferred embodiment of a pronged plate for use in the case of a fracture of the radius.

SPECIFIC DESCRIPTION

Figure 1:
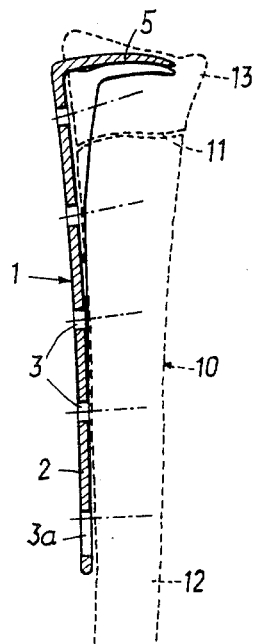
FIG. 1 shows a pronged plate according to the invention, in longitudinal section along the line I—I of FIG. 2.
Figure 2:
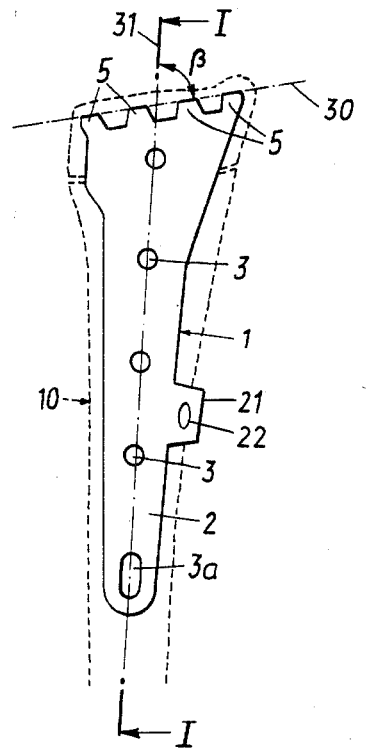
FIG. 2 shows the pronged plate according to FIG. 1 in front view and FIG. 3 shows the pronged plate according to FIGS. 1 and 2 in plan view.

As can be seen from FIG. 1, a pronged plate 1 according to the invention has a longitudinally extending, slightly curved part 2 which is formed with holes 3 for the insertion of screws. In its end region which is at the top in the drawing, the plate 1 is provided with four prongs 5 projecting at an angle of about 80°. As FIG. 2 shows, the plate 1 has a width which increases towards the prongs 5. Moreover, it is formed with five apertures 3, the lowest perforation 3a having the shape of a slot.

Figure 3:
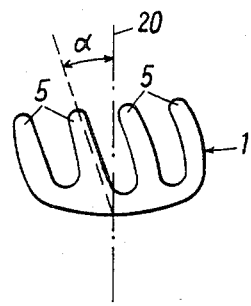

As can be seen from FIG. 3, the prongs 5 include angle α of about 20° with the first plane 20 which includes the longitudinal axis of the plate 1 and is generally perpendicular to the part 2, in contact with the shaft of the bone, of the plate 1. The axes of the prongs are longitudinal axes angularly extends from a face of a plate and generally lying in a plane transverse to the axis of the plate. The axes of these prongs define the angle α with the first axial plane as defined above. This effectively prevents the articular part from sliding off the prongs 5. For use on the right half or left half of the body, the prongs 5 can point respectively to one side or the other relative to the part 2, so that it is possible to speak of left-handed or right-handed pronged plates 1.

In FIGS. 1 and 2, a radius 10 is also shown in broken lines, in which there is a typical fracture 11 in the region of the part which carries the articulation, that is to say the part remote from the body. Since the part 13, which carries the articulation, of the radius 12 has a porous structure and since, moreover, the size of the possible support area for the plate 1 is relatively small, the latter is fixed in the fragment 13 carrying the articulation by means of the four prongs 5 which project from the plate 1 and are inserted into the fragment 13 carrying the articulation.

The plate 1 is fixed in such a way that initially bores for the prongs 5 are made in the fragment 13 with the aid of an aiming device, whereupon the prongs 5 are knocked into the fragment 13. Thereupon the plate part 2 of the plate 1 is fixed to the shaft 12 of the radius 10 by means of a screw passing through the lowest perforation 3a shaped as a slot. After checking the position of the plate 1 on the X-ray screen, a slight change of position of the plate 1 relative to the shaft 12 can be carried out by means of the slot 3a. Screws are then inserted through the remaining holes 3 into the shaft 12 of the bone. In doing this, the direction of the screw located nearest the prongs 5 is in particular selected according to the requirements of the particular fracture, i.e. in such a way, in the illustrative embodiment, that this screw includes an angle of about 30° with the prongs 5.

A plate of similar shape can also be used for different fractures, such as, for example, in the case of vertebral fractures. Of course, the size and shape of the plate, as well as the direction of the prongs, must be adapted to the intended use.

Additionally, it is pointed out that the plate part 2 can also be formed with a lateral lug 21 which is likewise provided with a bore 22. In FIG. 2, this lug 21 is shown. This lug 21 projects from the plate part 2, is curved and has such a length that the bone 10 is surrounded over about 90° by the plate part 2 and the lug 21.

The second plane 30 in which approximately the prongs 5 lie includes an angle $\beta$ of 65° to 80° with the line 31 connecting the bores 3 and the axis of the plate.

The lug 21 serves to receive an additional screw, by means of which, in the case of using the pronged plate 1 in the region of the lower arm, the ulna and the radius (the two bones of the lower arm) can be fixed together and thus positioned in a defined relation to accelerate the healing process.

Although not shown in the drawings, the main part 2 of the plate 1 may be bent slightly outwards before curving over into the prongs 5, so that an offsetting of the wider region of the plate is produced.

Although the preferred embodiment of the pronged plate has been described above, it will be appreciated that the invention is not limited thereto. Accordingly, any and all modifications, variations or equivalent arrangements which may occur to those skilled in the art should be considered to be within the scope of the invention as defined by the appended claims.

What is claimed is:

1. A pronged article for fixing bone parts in position together at a bone fracture in the region of an articulation, comprising an elongated plate having a longitudinal axis and adapted to lie along one of said bone parts, said plate being transverse to a longitudinal plane including said axis and having a plurality of prongs projecting transversely from one end of the plate, said plate having a plurality of apertures formed therein for receiving plate fixating means for securing said plate to said one of said bone parts, said plate being characterised by the improvement wherein the axes of said prongs, when extended to intersect said longitudinal plane, each include angles of between 10° and 30° with said longitudinal plane.

2. A pronged article claimed in claim 1 wherein said axes of said prongs adjacent said plate are substantially coplanar in a further plane which intersects said longitudinal plane with an included angle of less than 90°.

3. A pronged article as claimed in claim 2 wherein said included angle of said further plane is an angle of 80°.

4. A pronged article as claimed in claim 1 wherein said plurality of prongs comprises four prongs.

5. A pronged article as claimed in claim 1, wherein said plate over its entire longitudinal extent, has a width which steadily increases in the direction of the prongs, the width in the region of the prongs being at least 1.5 times that in the region of the other end.

6. A pronged article as claimed in claim 5, wherein said plate is bent outwards at its wider region.

7. A pronged article as claimed in claim 5 wherein said width in the region of said prongs is three times that in the region of said other end.

8. A pronged article in claim 1 wherein at least one of said apertures is provided for receiving a screw which can be inserted into an articular bone part, in a region directly adjacent to the prongs.

9. A pronged article as claimed in claim 1 wherein at least one of the apertures is shaped as a slot.

10. A pronged article as claimed in claim 9 wherein said at least one aperture is the aperture furthest away from said prongs.

11. A pronged article as claimed in claim 1 said axes of said prongs lie generally in a transverse plane which includes an angle of 65° to 80° with said longitudinal axis.

12. A pronged article as claimed in claim 1 wherein said longitudinally extending part of said plate is formed with a laterally projecting, curved lug which is provided with a bore.

13. A pronged article as claimed in claim 1 wherein said angle included by the axes of said prongs with said plane is an angle of about 20°.

* * * * *